United States Patent
Pahwa et al.

(10) Patent No.: US 9,534,840 B2
(45) Date of Patent: Jan. 3, 2017

(54) METHOD AND DEVICE FOR MOISTURE DETERMINATION AND CONTROL

(71) Applicant: BRY AIR (ASIA) PVT. LTD., Delhi (IN)

(72) Inventors: Deepak Pahwa, Delhi (IN); William Charles Griffiths, Palm Beach Gardens, FL (US); Marco Sammartini, Vanegono Inferiore (IT); Rajan Sachdev, Delhi (IN); Kuldeep Singh Malik, New Delhi (IN)

(73) Assignee: BRY AIR (ASIA) PVT. LTD., Delhi (IN)

(*) Notice: Subject to any disclaimer, the term of this patent is extended or adjusted under 35 U.S.C. 154(b) by 24 days.

(21) Appl. No.: 14/366,922

(22) PCT Filed: Dec. 19, 2012

(86) PCT No.: PCT/IN2012/000831
§ 371 (c)(1),
(2) Date: Jun. 19, 2014

(87) PCT Pub. No.: WO2013/093942
PCT Pub. Date: Jun. 27, 2013

(65) Prior Publication Data
US 2014/0345153 A1   Nov. 27, 2014

(30) Foreign Application Priority Data
Dec. 20, 2011 (IN) .......................... 3735/DEL/2011

(51) Int. Cl.
*F26B 5/16* (2006.01)
*F26B 21/08* (2006.01)
(Continued)

(52) U.S. Cl.
CPC ............... *F26B 5/16* (2013.01); *F26B 21/083* (2013.01); *F26B 25/003* (2013.01); *F26B 25/22* (2013.01);
(Continued)

(58) Field of Classification Search
CPC ................. F26B 5/00; F26B 5/16; F26B 7/00; F26B 9/00; F26B 11/00; F26B 21/00; F26B 21/01; F26B 25/00; F26B 25/003; F24F 3/00; F24F 3/1423; F24F 11/00; B01D 53/00; B01D 53/261
(Continued)

(56) References Cited

U.S. PATENT DOCUMENTS 3,259,995 A * 7/1966 Powischill .............. F26B 17/04
                                                       236/15 BC
3,765,100 A * 10/1973 Heidtmann ............. D06F 58/28
                                                       34/533
(Continued)

FOREIGN PATENT DOCUMENTS

DE    3929858 A1 * 3/1991 .............. F26B 21/04
EP    0 437 267 A1   7/1991
(Continued)

*Primary Examiner* — Stephen M Gravini
(74) *Attorney, Agent, or Firm* — Ladas & Parry, LLP (57) ABSTRACT

The present invention relates to a method for moisture determination and control using real time measurement of the moisture content of the material being processed. The present invention also provides a device that is used for moisture determination and control based on real time measurement of moisture content of a material being processed. The present invention is particularly suitable for controlling the moisture content of a material in a drying process, such as in a drying hopper, where the material moisture content is measured at an inlet and an outlet of the drying process. The drying process is further controlled by (Continued)

anticipating the drying load by measuring the moisture content of the incoming material to be dried.

18 Claims, 9 Drawing Sheets

(51) Int. Cl.
- *F26B 25/22* (2006.01)
- *G01N 33/44* (2006.01)
- *F26B 25/00* (2006.01)
- *F26B 17/00* (2006.01)
- *G01N 33/34* (2006.01)
- *G01N 33/36* (2006.01)

(52) U.S. Cl.
CPC ........... *G01N 33/442* (2013.01); *F26B 17/006* (2013.01); *F26B 17/007* (2013.01); *G01N 33/34* (2013.01); *G01N 33/36* (2013.01)

(58) Field of Classification Search
USPC ..... 34/330, 413, 524, 595, 282; 68/5 C, 5 R, 68/19, 20; 8/139, 149, 159; 95/10, 14; 96/111, 96/112
See application file for complete search history.

(56) References Cited

U.S. PATENT DOCUMENTS

| | | | |
|---|---|---|---|
| 4,507,875 A * | 4/1985 | Hirsch | G01N 7/00 236/44 C |
| 5,257,532 A | 11/1993 | Hayakawa | |
| 5,377,428 A | 1/1995 | Clark | |
| 5,592,754 A * | 1/1997 | Krieder | B01D 53/261 34/527 |
| 5,802,736 A * | 9/1998 | Klockenkemper | B31F 1/2813 156/64 |
| 5,937,535 A | 8/1999 | Hoffman | |
| 6,439,027 B1 | 8/2002 | Hiss, III | |
| 6,691,563 B1 | 2/2004 | Trabelsi et al. | |
| 6,807,750 B1 * | 10/2004 | Lewis | F26B 17/101 19/66 CC |
| 7,330,034 B1 | 2/2008 | Pelletier et al. | |
| 7,676,953 B2 * | 3/2010 | Magill | G01N 27/223 144/380 |
| 7,856,737 B2 * | 12/2010 | McMahon, Jr. | F26B 17/12 110/187 |
| 8,056,255 B2 * | 11/2011 | Smith | F26B 17/08 110/228 |
| 8,316,557 B2 * | 11/2012 | Burnett | E21B 21/066 175/207 |
| 8,919,007 B2 * | 12/2014 | Friess | F26B 5/06 250/231.1 |
| 2010/0275775 A1 * | 11/2010 | Griffiths | B01D 53/0454 95/18 |
| 2010/0300183 A1 | 12/2010 | Dasher et al. | |
| 2011/0006461 A1 | 1/2011 | Dasher et al. | |
| 2014/0317954 A1 * | 10/2014 | McCallum | F26B 21/06 34/565 |
| 2014/0345153 A1 * | 11/2014 | Pahwa | F26B 21/083 34/330 |
| 2015/0026995 A1 * | 1/2015 | Schaefer, Jr. | F26B 21/12 34/565 |
| 2015/0153051 A1 * | 6/2015 | Pahwa | F24F 3/1423 95/10 |

FOREIGN PATENT DOCUMENTS

| | | | |
|---|---|---|---|
| EP | 0 798 051 A1 | 10/1997 | |
| HU | WO 8301502 A1 * | 4/1983 | ............ F26B 17/122 |

\* cited by examiner

METHOD AND DEVICE FOR MOISTURE DETERMINATION AND CONTROL

RELATED APPLICATION INFORMATION

This application is a 371 of International Application PCT/IN2012/000831 filed 19 Dec. 2012 entitled "Method and Device for Moisture Determination and Control", which was published in the English language on 27 Jun. 2013 with International Publication No. WO 2013/093942 A2, and which claims priority from Indian Application No.: 3735/DEL/2011 filed 20 Dec. 2011, the content of which is incorporated herein by reference.

The present invention relates to a method for moisture determination and control using real time measurement of the moisture content of the material being processed. The present invention also provides a device that is used for moisture determination and control based on real time measurement of moisture content of a material being processed.

The term "moisture" in the context of the present invention is not intended to be limited to the conventional understanding of "water" but rather is intended to encompass all fluids, the presence or absence of which, may have an advantageous or deleterious effect on a manufacturing process and/or on the final product of such manufacturing process. By way of illustration, the term "moisture" is intended to encompass, water, solvents whether organic or inorganic, any other fluid that may impact on a given manufacturing process and on final product manufactured thereby.

BACKGROUND OF THE INVENTION AND PRIOR ART

The assessment and control of moisture content of natural or synthetic materials is considered important in several industries such as pharmaceuticals, food, agrochemicals, plastics, construction, mining, paper manufacture, catalyst manufacture, petrochemicals, semiconductors, etc. In several cases, the moisture content is taken as an indication of the quality of the product.

It is recognized that practically all manufacturing processes require strict control of the fluid levels therein, at times at ppm levels, in order to comply with quality requirements, regulatory standards, prevent defects in the final product of such processes, etc. For example, the presence of unwanted moisture (water) in granule manufacture in pharmaceuticals can have an adverse effect on the product in terms of agglomeration of granules, leading to rejection of product batches. Another example involves the treatment of polymeric materials. During the processing of various polymeric materials, it is imperative to regulate the level of hydrolysis such that the final product, whether in powder form or extrudate form or granular form is free of defects such as fines, fractures on the surface or internally etc. Similarly, resin processing is a technology in which it is imperative to control the levels of moisture present in the system so that molding of the resin products is rendered efficient and wastage of material is avoided. It is also imperative to control moisture levels during paper manufacture such that the final product has less than 3% moisture present.

As can be seen, different industries have different product moisture requirements, and in some cases optimal quality which requires the presence of ppm levels of moisture is not attainable without significant cost-increases in the manufacturing process and expenditure of high levels of energy.

Moisture content determination is generally done by two methods—direct and indirect. The former, viz. direct methods involve measurement of weight loss of the product using methods such as oven drying or chemical titration using Karl Fischer reagents. Direct methods generally provide a reasonably high level of accuracy, however, suffer from requiring off-line treatment. Thus, such methods are not suitable in industries where the level of automation is higher, and in fact even in other industrial methods suffer from the disadvantage of being energy inefficient and expensive.

Indirect methods of moisture determination involve the use of techniques such as electromagnetic wave measurement, the use of nuclear, dielectric or infra red sensors etc. While these methods provide contactless measurement, the applicants are unaware of any method by which sampling and averaging over the entire material volume has been achieved with significant degrees of accuracy, and also enabling control in real time. Such methods are known to provide for measurement online. However, the aspect of measurement and control proceeding concurrently and online or in-line has not as yet been explored.

Historically, methods of moisture level determination in manufacturing processes have involved off-line measurement. This has entailed stopping a process stream, removing a sample of the product stream, and determining the level of moisture therein, using equipment such as the Karl-Fischer reagent. Dependent on the readings obtained in the detection, the process parameters are then reset to ensure that the product stream achieves the required level of moisture presence or absence. As is evident, such processes suffer from a significant disadvantage in that they are not energy efficient, entail work stoppage and restart, and the levels of accuracy are not high.

For example, it was known that maintaining moisture content of organic resin materials at a constant level is important to ensure good quality of the resin products. Inappropriate levels of moisture content in resin materials being supplied to a moulding machine have resulted presence of such defects such as voids and silver lines in the product. It was conventionally known to dry such resin materials using a hopper dryer prior to supply of the materials to the moulding machine. This involved setting a fixed heating temperature and heating time for the hopper drier based on an estimation of the moisture content of the resin materials. The products are sampled and subjected to a titration analysis using a Karl Fischer reagent. While such methods do result in a reasonable degree of accuracy, they suffer from the attendant disadvantages of requiring off-line moisture measurement in a laboratory or by trained professionals, and are also not repeatable. As is evident, the stop-restart of the process is in itself a significant disadvantage in terms of energy inefficiency.

It is recognized that moisture content of materials is important in even food and agrochemical research and industrial applications. Generally, the drying techniques used in these industries involve oven drying based on drying samples under specific conditions of temperature and time depending on the material. However, such techniques are time consuming and are energy intensive. Additionally, the accuracy of such techniques is suspect due to differentials between the sample being tested and the mass distribution of the material in the product stream. Attempts have been made in such applications to utilize electromagnetic wave interaction for continuous measurement. While this method has one advantage of being non-contact, it is liable to fluctuations due to the variations in bulk density of the product stream. This requires that density also be continuously monitored separately, leading to enhanced energy and cost consumption, apart from making the measuring system extremely complex.

There are several prior arts in the field of moisture measurement or determination, including both online and offline measurements. Some of these are discussed below.

The requirement of moisture determination and control (emphasis added) in various industries will be discussed below with reference also to the art that is known in such industries, their advantages and their limitations.

In the field of ceramic forming materials, the use of extrusion processes is common. One type of an extrusion process that is used in this industry involves use of a ceramic-forming material that forms a plastic mix or "batch material". This is extruded through a die orifice to form a shaped article. Ceramic honeycomb-shaped articles having a multitude of cells or passages separated by thin walls running parallel to the longitudinal axis of the structure have been formed through extrusion and used as filters for a variety of applications, including particulate filters for combustion engines. This process requires control of a number of parameters so that the desired article maintains its post-extrusion form. The parameters include, for example, the particular composition of the mix that makes up the batch material, and the moisture content of extruded logs that can subsequently be dried and fired to form a ceramic article. A batch material having insufficient moisture will not extrude properly and could lead to the formation of cracks, including invisible microcracks, in the final article. On the other hand, an organic batch material having too much moisture will also not extrude properly and could lead to deformation of the extruded article.

US Patent Publication 2010/300183 discloses an in-line method of measuring the moisture content of ceramic material within an extrusion system used to form ceramic articles. The method of this disclosure comprises arranging, at least one radio-frequency (RF) sensor system having an RF antenna relative to the extrusion system, and generating through the RF antenna an RF field that resides substantially entirely within the ceramic material; in response to the RF field interacting with the ceramic material, generating in the RF sensor system a signal SM representative of a raw moisture-content measurement of the ceramic material; generating calibration data by performing RF moisture-content measurements on samples of the ceramic material having different known moisture contents; and establishing a calibrated moisture-content measurement using the raw moisture-content signal SM and the calibration data. The method of this disclosure and the subsequent development thereof in US 2011/0006461 both rely on removal of a sample and testing thereof. Therefore, effectively, while the measurement levels are deemed significantly accurate, the control mechanism is still off-line. Therefore, the method would involve stoppage if alterations are to be done in the moisture levels. In addition, product could be made off-specification for a time until the process is adjusted.

U.S. Pat. No. 5,377,428 relates to papermaking drying processes and apparatus for producing paper with low moisture content. While this document states that it also relates to a control mechanism, the mechanism is specific to the paper manufacturing industry and is dedicated to measurement to 3% levels of moisture. The system of this disclosure comprises cross-direction drying means controllable to modify the temperature across the web, temperature detection means for determining the cross-direction temperature profile of the web, and modulation means for controlling the cross-direction drying means in response to variations in the temperature profile to produce an optimally uniform cross-direction temperature profile. The temperature detection means includes a high temperature detection means positioned where at least a portion of the web can have a temperature above the boiling point of water and, optionally, a low temperature detection means located where an entire cross-direction strip of the web will be at a temperature below the boiling point of water. Drying rate prediction means are further included to predict the drying rate of the web as a function of observed temperature in locations proximate to the low temperature detection means. The modulation means is responsive to signals from both the high and low temperature detection means to produce a substantially uniform cross-direction web temperature profile near the high temperature detection means. The drying control method of the present invention produces a substantially flat, uniform cross-directional profile by detecting the cross-direction web temperature, monitoring the cross-direction temperature profile as the web is dried, and controlling the rate of drying the web to insure that the web temperature is maintained at a substantially uniform optimum temperature and flat cross-directional profile. As can be seen, this system is limited in its applicability to paper manufacture and is entirely dependent on temperature measurement to enable control.

U.S. Pat. No. 6,439,027 discloses a method for gas moisture measurement, and more particularly, to particulate mass measurement instruments operable to measure the moisture content of effluent gas for real-time adjustment of isokinetic sampling during measurement of the mass of particulate matter flowing in a stack or other exhaust conduit. While the method appears to comprise moisture content measurement of the effluent gas in real time; obtaining an isokinetic sample of a portion of the effluent gas based on real-time moisture content measurement of the effluent gas, including a step of determining a proportion of water vapor by volume of the effluent gas, the actual measurement method appears to be offline is based on an isokinetic measurement.

U.S. Pat. No. 7,330,034 discloses a method and a system for moisture measurement in cotton bales. The process of this disclosure comprises measuring the moisture content and the mass-moisture content of materials without requiring air reference or calibration sequence. A microwave signal is split into a reference and a transmission signal, and the reference signal is applied directly to the phase detector, whereas the transmission signal is first transmitted through the sample before being presented to the other side of the phase detector. This measurement provides a phase-constant measurement that is due to the dielectric characteristics of the material under test. The system measures the material's phase-constant across a band of frequencies. The slope of the phase-constant versus frequency is then utilized to predict the density of the material which is then combined with the corrected phase-constant measurement to calculate the moisture content of the material. This disclosure is limited to determination of moisture content and does not provide on-line solutions for moisture content control.

U.S. Pat. No. 6,691,563 discloses what apparently is an invention to provide a method and apparatus for determining moisture content in any particulate or granular material at any radio-frequency and temperature without knowledge of bulk density from a single moisture calibration equation. However, the method of this disclosure requires the measurement at at least two points, and is moreover limited to measurement of dielectric constants. In addition, it is not very clear whether the method truly provides for absolutely on-line and continuous control. The method does appear to provide for measurement of moisture content, but the control algorithm would appear to have a significant time lag due to its complexity, and the need for multiple measurements.

The food processing industry is subject to stringent norms on the level of moisture content that is permitted in any given product. It is desirable in this area of technology to be able to guide the composition of food materials as to moisture content in order that tight control of processing can be maintained to assure efficient operation and efficient use of resources. The moisture content of liquid, semi-solid, or powdered food material has hitherto been determined by a variety of methods. For example, it is known to use a gravimetric method using either a vacuum or a microwave oven. Both variations are inconvenient to use when regular measurement of the moisture content of, e.g., hundreds of samples is required. The vacuum oven variation also requires undesirably long measurement times for on-line food processing. Other methods include measuring reflectance or absorption or some other parameter as an indirect indication of moisture content. However, all prior techniques have been found to lack at least one of several requirements for conveniently and meaningfully measuring moisture content of food materials. Such requirements include, illustratively, high temperature tolerance, short time to make a moisture content measurement of a sample, ease of calibration, and substantially no contamination between sensor and food system.

U.S. Pat. No. 5,257,532 discloses a method where moisture content measurements are alleviated by measuring the temperature-difference versus logarithm-of-heating-time response of a sample of a predetermined material during a predetermined heating time interval, determining the slope of that response at a portion thereof of approximately maximum slope, determining a temperature parameter related to the temperature at the start of heat application, and calculating the moisture content of the sample as a function of that slope and that temperature parameter. However this method also appears to require off-line testing of a sample, or at the very least involves a time lag between measurement, and then introduction of the control means, which may be not of significant use in increasingly automated industrial processes.

Apart from the above, there are several prior art disclosures known for moisture determination in different fields of technology such as soil testing, mining, agro-chemicals, polymer processing etc. However, the prior art known to applicants appear to focus on off-line testing followed by moisture content control, or alternatively have serious shortfalls in terms of moisture content levels that can be measured and controlled, as well in the time lags between measurement and control. The focus in the art appears to have been on off-line measurement strategies due to the relatively high levels of accuracy required, and also appear to have been industry specific. Indeed, applicants are not aware of a single measurement and control methodology which is universally applicable irrespective of the industry, and which provides measurement levels at the ppm range and provides for simultaneous control of moisture content.

OBJECTS AND SUMMARY OF THE INVENTION

It is an object of the invention to provide a method for on-line moisture measurement and control in an industrial process wherein high levels of accuracy are required as well as high levels of energy efficiency.

It is another object of the invention to provide a direct method for moisture content determination and control whereby material from a drying process is provided at the required conditions using the minimum amount of energy in the drying process.

Other objectives of the invention include providing material from the drying process at the maximum possible drying rate, and providing material from several parallel drying processes at the same quality using a single central device providing a drying utility to each of the parallel drying processes.

It is another object of the invention to provide a universal on-line moisture determination and control method which is applicable not only in industries where moisture has to be removed from the process but also in industries wherein moisture may require addition to ensure that the product stream has the requisite/desired moisture content.

While the invention is described below with reference to drying processes, it must be understood that it is applicable to any process where moisture control is essential and encompasses systems where moisture content has to be increased to prevent excessive dryness in the product stream. As stated above, while some embodiments of the invention are described with reference to water as the 'moisture', this term also encompasses the presence of any fluid, such as solvents etc. in a system whose presence and quantity play a role in the system.

In one embodiment the invention comprises a method for direct control of a drying process based on real-time measurement of the moisture content of the material being dried tough one or more sensors provided at pre-determined locations in the drying process, collecting and collating the information obtained in real time and in dynamic mode, and transmitting said information to a control means, processing said information in real time, regulating moisture content in said drying process based on input from said control means.

In another embodiment of the invention, the moisture content of the material leaving the drying process is monitored and the operating parameters of the dehumidifier are controlled to maintain the desired moisture content. The controlled parameters may include the dehumidified air volume, temperature and humidity supplied to the hopper, the volume and temperature of heated air supplied for reactivation of the desiccant, and the frequency of reactivation of the desiccant material.

In another embodiment of the invention, the operating parameters of the dehumidifier are adjusted based on the real-time measurement of the flow rate of material entering and/or leaving the drying process. In this way the operation of the dehumidifier may be adjusted in anticipation of a change in drying load due to the change in flow rate of the product material.

In still another embodiment of the invention, the operating parameters of the dehumidifier are adjusted based on the real-time measurement of the moisture content of the material entering the drying process. In this way, the operation of the dehumidifier may be adjusted in anticipation of a change in drying load due to the change in moisture content of the entering material.

In an additional embodiment of the invention, the moisture content of the material may be measured at one or more intermediate points during the drying process to adjust the drying parameters for optimum performance.

In yet another embodiment of the invention, the real-time input data acquired in all the embodiments listed above are used in a comprehensive control algorithm for the dehumidifier and process air system.

In an additional embodiment of the invention, the input data and control algorithms described herein are used to control a dehumidifier providing drying capacity to two or more parallel drying processes. The control may include overall adjustment of the operation of the dehumidifier and process air system and individual adjustment of the drying force supplied to each drying process. The adjustments may include the volume, power level and temperature of the drying force provided.

The embodiments described above are based on the drying of granular materials in a bin or hopper, but it will be understood by one skilled in the art that the same concepts may be applied to other materials and drying processes. These processes may include energy transfer to the dried product by means of radiation.

In another embodiment, the device of the invention is provided with two sensors, the first sensor being provided at an inlet position of the dryer to provide information in respect of the average moisture content measured during loading of the material into the dryer, the second sensor being provided at an outlet position on the dryer to supply information on the moisture content after the drying process, a two-way valve being provided to allow the return of non-conforming material back to the dryer for a further period of drying if the measured value does not conform to the desired product.

In another embodiment of the invention, the values generated by the two sensors are utilised by the control means to minimise the power requirements of the process, using integral calculation of multiple parameters.

In yet another embodiment of the invention, the control process comprises control of any one or more of temperature set point, drying time, dew point adjustment, air flow speed, rotor speed, nitrogen set point, nitrogen filtering station, desiccants tower switch, desiccant regeneration, microwave power generators, filters replacement time, methane gas regulation, steam generator control.

The invention also provides a moisture determination and control mechanism for food or feed applications wherein said system enables control of the dosage instrument for the feed stock, the mixer and the homogenizer In another embodiment of the invention, the device and the method of the invention are implemented with a single sensor.

In another embodiment of the invention, the program implemented is a fuzzy logic or neuro-fuzzy system (NFS) to allow a corresponding adjustment of the parameters of the dryer to "almost human" control logic.

BRIEF DESCRIPTION OF THE DRAWINGS

These and other embodiments and advantages of the present invention will become more fully apparent from the following description and accompanying drawings where.

DETAILED DESCRIPTION OF THE INVENTION

The invention provides a method for direct control of drying processes. The present invention also provides a device where the moisture content of a product that is being processed can be modified at differing points of time/location in the process stream depending on specific moisture requirements at such time/position, based on real time measurement of the moisture content therein.

The method of measurement may include indirect methods which do not require contact with the material being dried, such as measurement of the electrical capacitance, absorption of radiation or the like of a moving stream of the material being dried. The moisture content of the material being dried may be measured at the discharge of the drying process, the inlet of the drying process, and/or at intermediate locations during the drying process.

Drying is defined as the removal of an unwanted component (such as moisture) from the material being dried. The unwanted component may be water, ice, a solid or liquid organic solvent or a mixture of chemical compounds. Energy and driving force for the drying process may be provided by direct contact with a secondary fluid such as air or an inert gas, or by indirect transfer of energy to the dried product via electromagnetic radiation at any frequency from radio and microwave through infrared, visible and ultraviolet spectra. The material being dried may be granular in form such as sugar, plastic pellets or the like, material that enters the drying process as a liquid but leaves as a solid in a spray- or flash-drying process, or solids that are passed through the drying process as a continuous sheet or web or conveyed through the drying process on a belt, trays or the like.

The unique feature of the current invention is the use of the measured moisture content of the material and using this data to control in a direct manner and on a real time basis the means provided to either dry or add moisture to the system. For example, in a drying process, the variables controlled may include the flow rate, temperature, pressure and humidity of a secondary drying fluid such as air, mass flow rate of the material being dried; and/or heat input via radiant sources such as RF, microwave and infrared.

Many industrial processes require the removal of moisture (water) from a material during the process. This disclosure is based on the removal of water (drying) from a material but it will be understood that the same concepts can be applied to the removal of other chemicals (such as solvents) from a material being processed.

The removal of water from a material is frequently an energy-intensive process. The final moisture content desired in a material frequently requires exposure to dehumidified air to achieve the desired final moisture content. The required air humidity is frequently lower than can be achieved with typical refrigeration-based dehumidification equipment. Removal of moisture from a material usually involves a change of phase of the water from a liquid or solid to a vapor. This change-of-phase requires a significant energy input, about 1000 BTU/lb for water. The drying of materials in an industrial setting typically requires a temperature- and humidity-controlled environment to achieve the desired moisture content in the material being dried. Sometimes radiant energy such as microwaves or RF radiation is used to provide a portion of the energy required to evaporate the water from the material.

Generally the lower the final moisture content desired in a material, the more energy intensive the drying process becomes. A good example is the drying of plastic pellets before they are fed to processing equipment such as extruders, injection molding machines or the like. The common plastics have some affinity for moisture that may be absorbed or adsorbed from the surrounding environment, and even tiny traces of water in the pellets will cause defects in the products from the equipment. To prevent this, the pellets are dried before being fed to the processing machines. The pellets are typically dried by passing warm dry air through the pellets while they are contained in a hopper above the processing equipment. Extremely dry air is needed to assure that the plastic pellets are dry enough to enter the processing equipment. The drying air must be far drier than can be produced by typical air-conditioning equipment so a desiccant dehumidifier is typically used in a closed-loop air system to produce the dry air needed to assure the dryness of the pellets. The desiccant dehumidification equipment has high energy consumption at its design load conditions, but these load conditions seldom occur because of the variation in the moisture content of the pellets entering the hopper and variations in the production rate of the processing equipment. At present these dehumidification units either are typically operated continuously at full energy input or are controlled to deliver air to the drying hopper at a constant low humidity level regardless of the moisture contained in the pellets entering the hopper. This causes the energy use of the dehumidifier to be higher than necessary. With the present invention the operation of the dehumidifier is at least partially controlled by real-time non-contact measurement of the moisture content of the plastic pellets entering the processing equipment, and may also be at least partially controlled by real-time non-contact measurement of the moisture content of the pellets entering the drying hopper and at one or more intermediate points within the hopper. The typical expected energy savings in this type of application are expected to be in the range of 10% to 50% or more.

In the method of the invention when applied to a dehumidifier controlled process, the moisture content of the material leaving the drying process is monitored and the operating parameters of the dehumidifier are controlled to maintain the desired moisture content. The controlled parameters include the dehumidified air volume, temperature and humidity supplied to the hopper, the volume and temperature of heated air supplied for reactivation of the desiccant, and the frequency of reactivation of the desiccant material.

The operating parameters of the dehumidifier may also be adjusted based on the real-time measurement of the flow rate of material entering and/or leaving the drying process. This enables the adjustment of the dehumidifier operation in anticipation of a change in drying load due to the change in flow rate of the product material.

The operating parameters of the dehumidifier may be adjusted based on the real-time measurement of the moisture content of the material entering the drying process. In this way, the operation of the dehumidifier can be adjusted in anticipation of a change in drying load due to the change in moisture content of the entering material.

The moisture content of the material may be measured at one or more intermediate points during the drying process to adjust the drying parameters for optimum performance.

The real-time input data acquired in all the embodiments listed above are used in a comprehensive control algorithm for the dehumidifier and process air system.

The input data and control algorithms described above may be used to control a dehumidifier providing drying capacity to two or more parallel drying processes. The control includes overall adjustment of the operation of the dehumidifier and process air system and individual adjustment of the drying force supplied to each drying process. The adjustments include the volume, power level and temperature of the drying force provided.

The embodiments described above are based on the drying of granular materials in a bin or hopper, but it will be understood by one skilled in the art that the same concepts may be applied to other materials and drying processes. These processes may include energy transfer to the dried product by means of radiation.

The device of the invention may be provided with one or more sensors. In one embodiment, the device uses two sensors. The first sensor is provided at an inlet position of the dryer. The inlet sensor provides information in respect of the average moisture content measured during loading of the material into the dryer. The program that is implemented is preferably a fuzzy logic or neuro-fuzzy system (NFS) to allow a corresponding adjustment of the parameters of the dryer to "almost human" control logic.

The second sensor is provided at an outlet position on the dryer. This sensor supplies information on the moisture content after the drying process. A two-way valve is provided to allow the return of non-conforming material back to the dryer for further drying if the measured value does not conform to the desired product. If the material conforms to the required drying parameters, then the product stream is forwarded sent to the next stream of production process. The two sensors collect moisture data in order to automatically control operating parameters of the dryer. An important feature of the invention is that the values generated by the two sensors are utilised by the control means to minimise the power requirements of the process. This is generally done using integral calculation. This process of regulation includes, depending on dryer technology: temperature set point, drying time, dew point adjustment, air flow speed, rotor speed, nitrogen set point, nitrogen filtering station, desiccants tower switch, desiccant regeneration, microwave power generators, filters replacement time, methane gas regulation, steam generator control.

In another example relating to food/feed application, the system also controls the mixer, homogenizer, dosing of vitamins and proteins. For example, where the food application relates to addition of sugar, the application dryer regulates the drum speed and material flow-rate settings, usually related to product moisture content. The outlet sensor therefore ensures the exact crystallization and moisture content required by regulatory measures.

The device (and the method) of the invention may also be implemented with a single sensor. For example, in feed/food applications dryers, the inline moisture measurement is installed on the outlet of the dryer and is used to regulate the exact quantity of all the additives needed for the product, sensitive to moisture contained in the products. The drying power is regulated according to the dryer output. In plaster/cement/marble-powders manufacture, the sensor is applied to the output of the dryer and adjusts the water addition which is usually introduced by measuring the discharge moisture content. Some dryers are, provided with a mixing station integrated in the dryer itself. This embodiment ensures that the minimum amount of water is required. Additionally the dryer can adjust water temperature and set point temperature.

In moulding application/multiple system dryers, the sensor dryer outlet supplies information on the moisture content after the drying process, of the valves distributing the product downstream. If the measured value does not conform to the desired product, a diverting valve will allow the return of the non-conforming material back to the dryer for a further period of drying. This is particularly useful in the use of polyamides, since this recirculation avoids the need for a separate second time drying process, and thereby avoids deterioration of the polymer. This application on dryers ensures a quality assurance for the moisture content of the product without any contamination which can happen if the dryer air is too dry. In the embodiments where a dehumidifier system is used, the invention relies on providing means to continuously vary the amount of air that will bypass the desiccant wheel, out of the total process flow dependent on the input from the control means connected to the one or more sensors. The reduction in process flow through the desiccant unit generally tracks the change in instantaneous moisture loads in the dryer system or the drying process. This is also equally applicable to a situation where the process being controlled is not a drying process but is an industrial process where moisture content must be maintained at a predetermined level. When the process flow through the desiccant wheel is reduced, it is no longer necessary to retain full regeneration flow through the reactivation sector of the wheel. Where the regeneration flow is correspondingly reduced in some defined correlation, a considerable reduction is achieved in regeneration energy usage.

The control function enables the user to continuously reduce or increase the regeneration air flow rate based on the continuously varying process flow rate through the process sector. The use of use variable speed drives, based on several known methods, allows continuous varying of reactivation air flow. Similarly, this technology can also be used for continuous speed variance of the rotational speed of the wheel, also through a correlating control function.

In a typical process drying/dehumidification system, the ambient air is passed through a cooling coil to reduce the moisture load and is cooled. A bypass damper modulates the airflow to be passed through the desiccant wheel and the remainder through the bypass. The mixed air is passed over heating/cooling sources and is tempered depending upon the requirement of the supply air. The regeneration flow is also controlled with the help of a damper generally positioned after the regeneration blower. The regeneration heat input can be electric, steam, gas burner or from a variety of heat sources that can elevate the temperature based on the specific design of the unit. This temperature is controlled by thermostat. Based on the conditions required in the drying bin, the mixed air is passed over a process heat input to provide the necessary drying temperature. The return air is cooled through a cooling coil and passed through the process sector and optionally the purge sector of the rotor. The face and bypass damper is used to control the flow that bypasses the dehumidifier. Air exiting the purge sector is recycled and mixed with the return air upstream of the cooling coil. This enables the dehumidifier to deliver drier air. The reactivation inlet temperature is controlled with a thermostat.

The above exemplifies one embodiment wherein a smart dehumidifier system can be used to implement the method and device of the present invention in a drying process.

Figure 9:
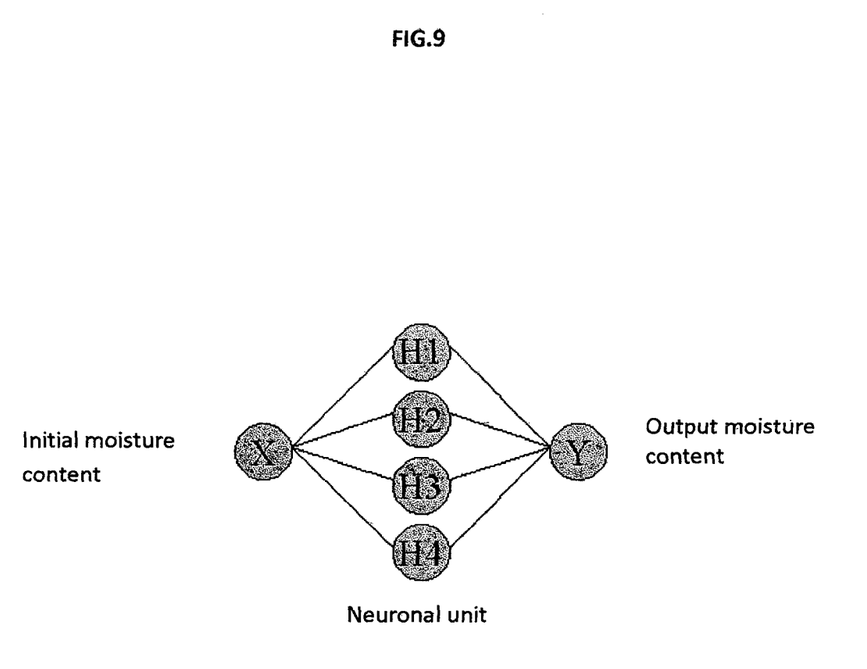
FIG. 9 is a schematic depiction of one of the moisture measurement and control algorithms that are used in the method of the invention utilizing a neural network.

FIG. 9 is a schematic depiction of a moisture measurement and control algorithm that may be utilised in the method and device of the invention, which involves the use of multiple moisture sensor means. This algorithm is predicated on the fact that a parameter that characterises the drying time and controlled drier variables of a product is dependent on its initial value of the moisture content and the distribution of the moisture in raw material, and is normally not homogeneous. Mapping of the moisture profile of the material loaded in a drier is an important parameter for control of the dryer stage components. A sensor measuring the moisture provides data to neuronal networks capable of performing extrapolation of correlations between data sets that are apparently random. In practice, the system conditions the neural network with a succession of time-series data of the phenomenon to be expected so that output and drier parameters converge to a certain value or to a specific configuration wherein the system is in effect a deterministic machine.

The formula of training used in this associative memory is the Hebb rule:

$$DW(j,k)=P(j)*P(k)*t$$

where:
delta W (j, k)=variation of the weight of connection between the neuron H1 and the neuron H2 . . . Hn
P(j)=output of neuron H1
P(k)=output of the neuron H2
t=factor or learning rate The algorithm described above can be utilised with suitable modification to various industrial applications, including reduction in the number of neurons. Each neuron represents a signal obtained from a moisture sensor, which in turn is collected, collated with other collected data, and a final determination made of the levels of moisture present versus the levels of moisture required, prompting the control means to send appropriate output signals to either add moisture or hasten the drying process, as may be required.

This methodology can be applied in each of the embodiments described hereinbelow. While the embodiments are described in the form of examples, they are truly descriptive of the method of the invention.

EXAMPLE 1

Drying of Engineering Polymers

Most engineering polymers, such as ABS, PA, PC, PET, PBT, PUR, and the like have polar groups inside the chemical chain structure. Those groups are responsible for the hygroscopic nature of the pellets. To produce high quality parts from hygroscopic plastic materials, it is mandatory to keep the moisture content of the processed material below an upper limit for the specific product. Otherwise, the residual water causes problems during processing and decreases structural and mechanical properties. Dimensional stability, increasing mechanical, acoustical and chemical properties of the products are some properties, which are influenced by moisture. Compounds based on polymers that are not themselves hygroscopic can sometimes cause problems because of hygroscopic additives.

Drying requires a lot of energy. Process parameters are set based on specifications from the producer of the raw material. These parameters are independent from the moisture of the raw material. Consequently, this leads to a higher energy consumption than is necessary and to fluctuations of the residual moisture. Very often companies over-dry material (using higher temperature and longer drying time) to avoid any possible problems during the moulding or extrusion.

Figure 1:
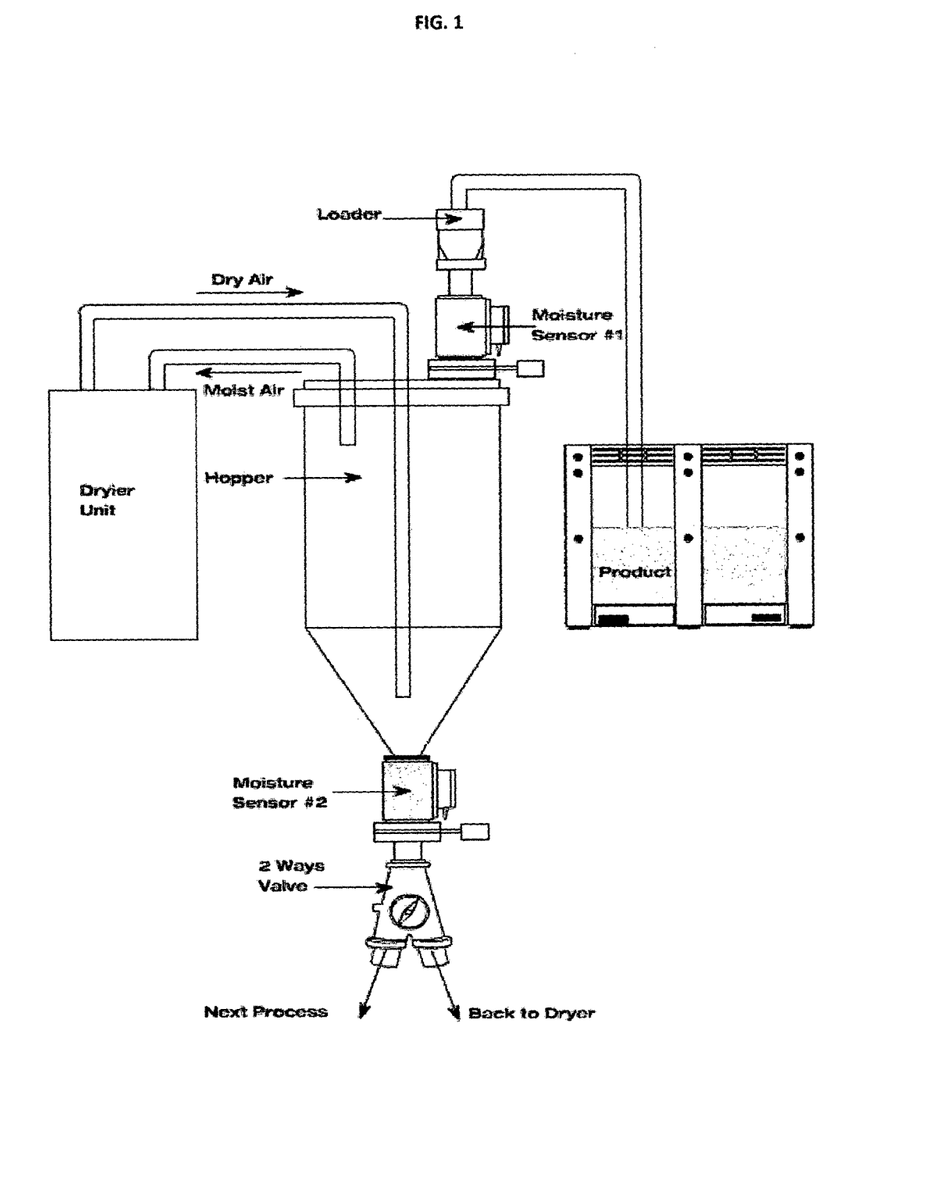
FIG. 1 is a schematic depiction of the use of a dehumidifier unit to control a hopper operation using the method and system of the invention in the embodiment discussed in Example 1.

FIG. 1 shows a dehumidifier using the control method and apparatus of the present invention. The control method and apparatus includes a microprocessor central controller, PLC or similar controller. The objective of this particular control arrangement is to maintain moisture content within the specification required for moulding and/or extrusion at the hopper outlet. The moisture level of outlet dried material values may be variable based on different plastic/resin types. To achieve and maintain the dried moisture level values at the hopper outlet will require control of reactivation heat energy, process airflow and process outlet heat energy which shall be optimized on the basis of control loop/logic.

Figure 2:
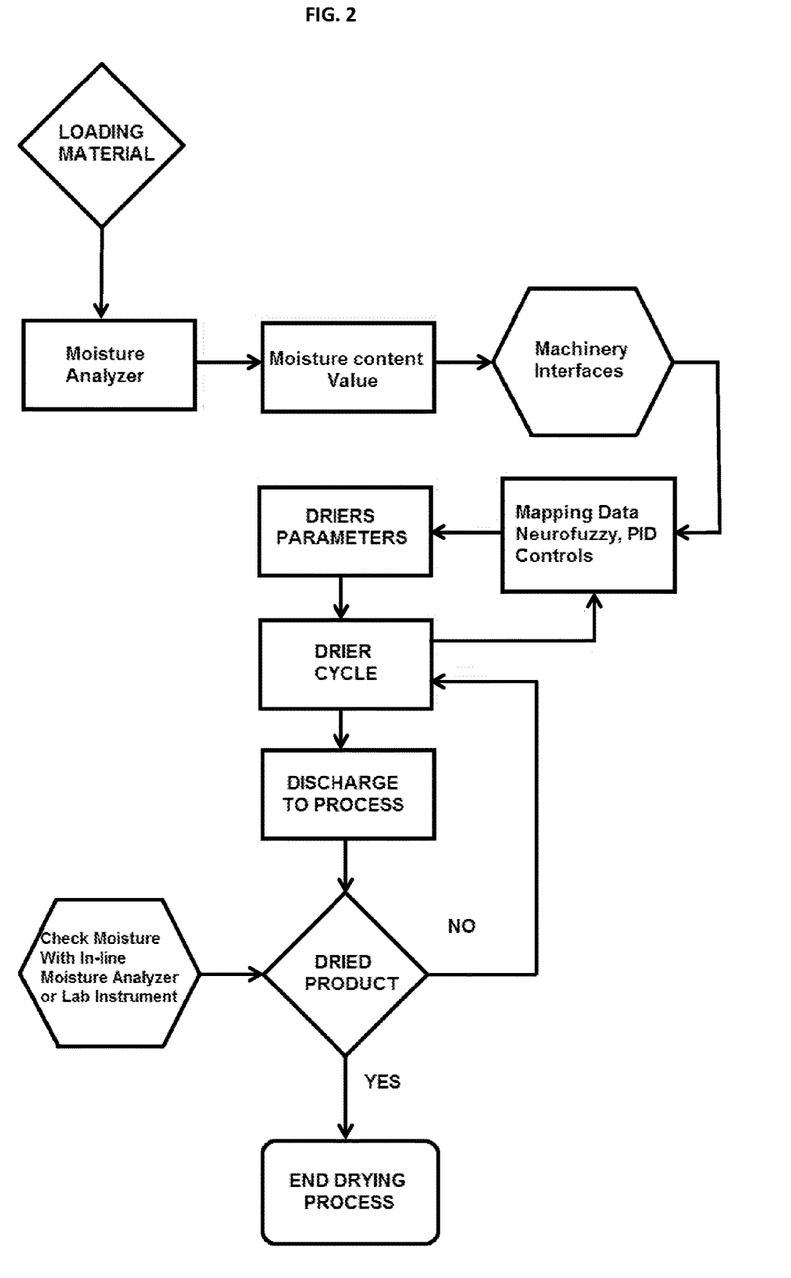
FIG. 2 is a operational flowchart for the embodiment of a hopper operation discussed in Example 1.

Controlled variables may include one or more of the following in any combination:
Heat input to reactivation air
Reactivation fan speed (to control reactivation airflow)
Process fan speed (to control process airflow)
Heat control to process air
Cooling coil at process inlet
Wheel rotational speed
Regeneration of Desiccant beads/Desiccant tower switch
Nitrogen dosing FIG. 2 is the operational flow chart that depicts the practice of the method of the invention using the device of the invention. The loaded material is analysed to determine the moisture content. The material is then fed to the machinery interface, and the data collected is mapped using neurofuzzy controls and the algorithm described hereinabove. The drying parameters are then set using the control means, which could include a desiccant dehumidifier mechanism as is described in FIG. 7. Once the drying parameters are set, the drying cycle commences, following which the product is discharged to the process, where if desired, further drying may be carried out and monitored using multiple sensors. The dried product is again checked for moisture content. If the content meets the desired value, the drying process is ended, and if not, the product is recycled back to the drying cycle. Through the process, the moisture levels are measured in-line and checked in-line enabling real time measurement of moisture and real-time control thereof without requiring stoppage of process, or even time consuming and expensive methods such as isokinetic measurement.

EXAMPLE 2

Dehumidification System Controlled Using Device of the Present Invention

Figure 3:
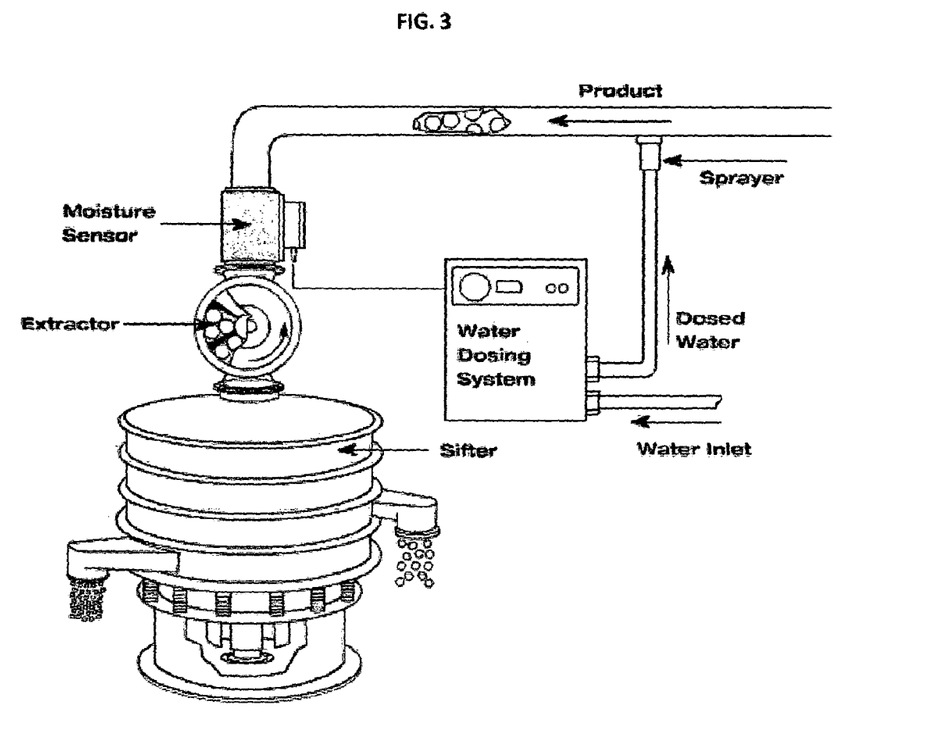
FIG. 3 is a schematic depiction of a moisture addition process wherein the use of a single sensor enables determination and control of moisture content as is described in the embodiment discussed in Example 3.

FIG. 3 illustrates the dehumidifier using the control method and apparatus of the present invention. The control method and apparatus includes a central controller, typically a programmable logic controller (PLC), or similar controller. The objective of this particular control arrangement is to maintain moisture level less than or equal to 100 ppm at the hopper outlet for dried Nylon 6 pellets/granules. The moisture level of outlet dried material values are a function of the different plastic/resin types and can vary. Achieving and maintaining the dried moisture level values at the hopper outlet requires control of reactivation heat energy, process airflow and process outlet heat energy, which is optimized on the basis of control loop/logic.

Controlled variables include one or more of the following in any combination:
Heat input to reactivation air
Reactivation fan speed (to control reactivation airflow)
Process fan speed (to control process airflow)
Heat control to process air
Cooling coil at process inlet
Wheel rotational speed

EXAMPLE 3

Dehumidifier in Product Size Control

In applications such as glass micro-beads, marble, choke, cement, construction material requires sifting to reach the desired dimensions. This is generally achieved through a Roto-sifter or vibrating sifter in the production stream. The process speed is strictly dependent on the moisture content as the quality and size of the sifting is regulated by the speed of the process, Moisture content in those materials causes them to tend to stick in the sifter. After the process of grinding, normally the material is dried or wetted sometimes to reach the right moisture to achieve the best production speed and the right size of the powder.

FIG. 3 illustrates the control method and apparatus which includes a microprocessor, PLC or similar controller. The moisture sensor is interfaced directly with. the production stream to regulate the speed of the sifter, the transportation, the extractor speed, water sprayers and/or other devices in the stream production line.

EXAMPLE 4

Moisture Control in Load Control

Figure 4:
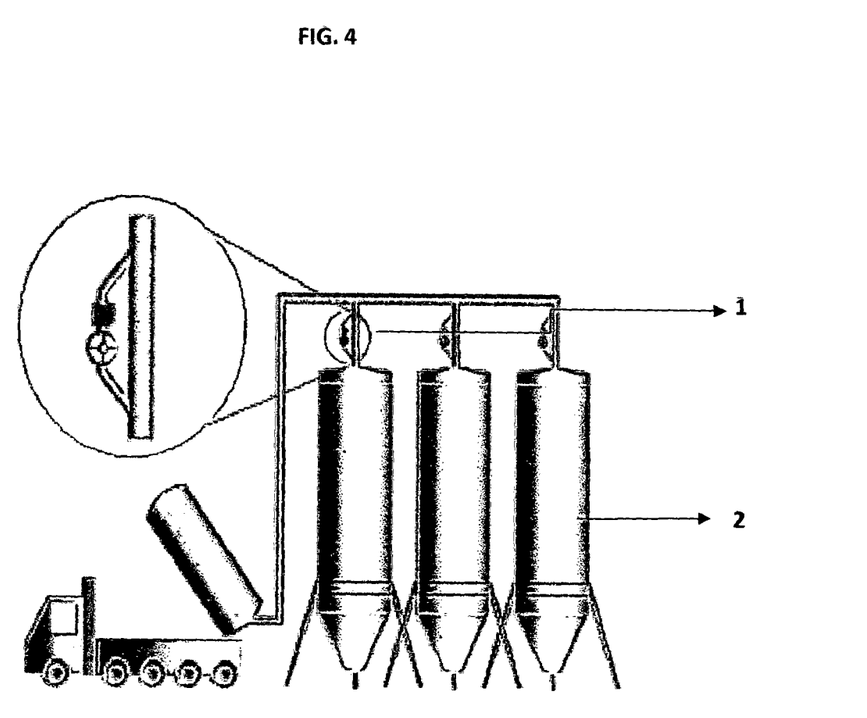
FIG. 4 is a schematic depiction of an application of the method and device of the invention in the field of load control, wherein the moisture specifications are provided by the supplier. This is discussed in the embodiment disclosed in Example 4.

FIG. 4 exemplifies an application of the method and device of the invention when applied to load control by an end user of a product in accordance with the specifications of the supplier. It is recognised that in both organic products and synthetic products, the humidity value at delivery is an important parameter for the quality or the subsequent processing. Typically, in the art, samples of a few grams are taken for testing, to verify the conformity of the product delivered. In the application of the method of the invention, an apparatus is used to measure moisture to control the product at the entrance of the storage silos. The system uses a moisture analyzer (1) connected with a loading control and by mapping the initial moisture the data generated is used as a parameter for the initial processing in the drier, prior to entry into the storage silo (2).

EXAMPLE 5

Moisture Control Process for Organic Food and Dyestuff Industries

Figure 5:
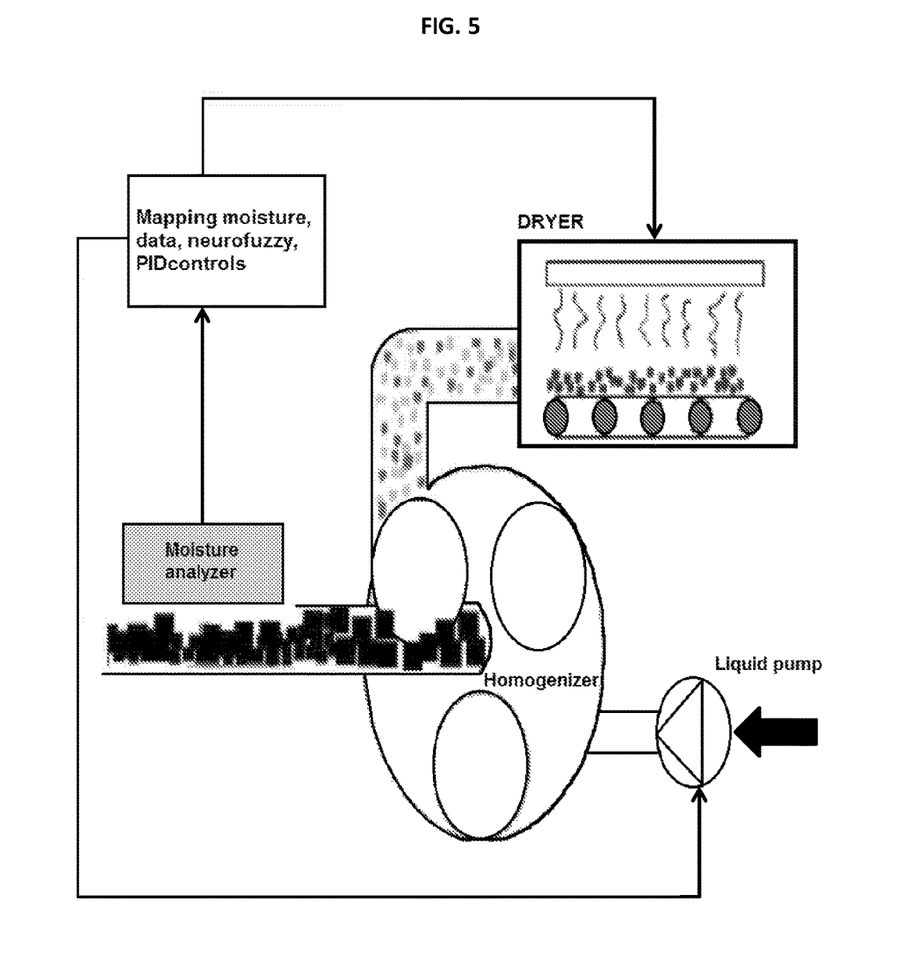
FIG. 5 is a schematic depiction of a moisture control process when used in organic food and general dyestuff industries. This is discussed in Example 5.
Figure 6:
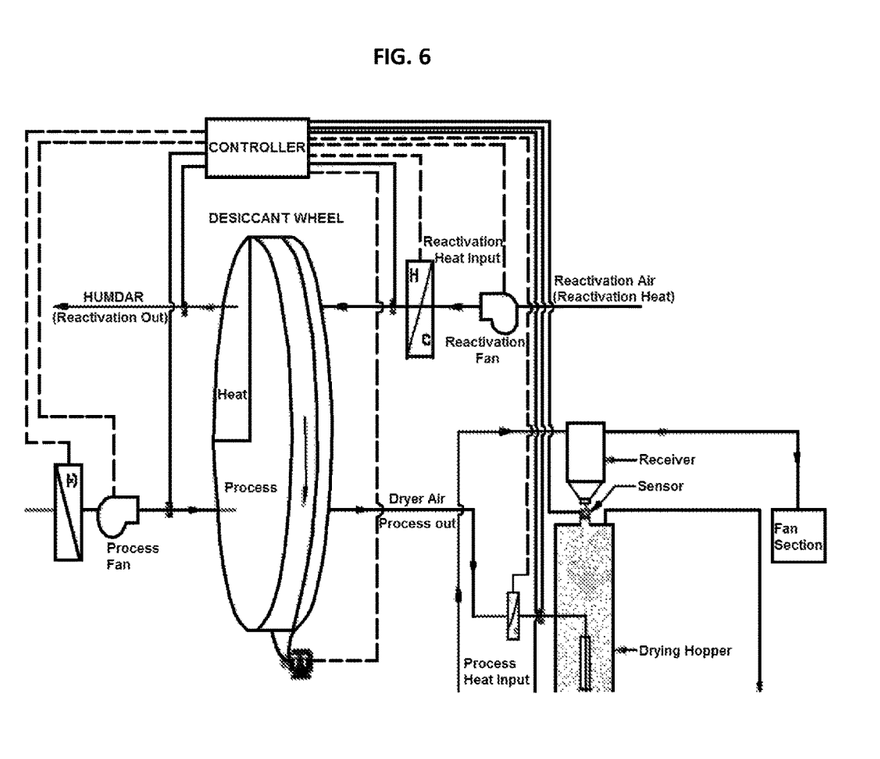
FIG. 6 illustrates the dehumidifier using the control method and apparatus of the present invention using a desiccant wheel. This is discussed generally in Example 1.

Typically, organic food and in general foodstuff including pet food need to be dried and moisture controlled during the production process. The materials are subjected to moisture control for two main reasons: rotten product, mildew and production problems, vitamins, proteins degradation. During the production process the product needs to be humidified with water or vapor to allow the right mix water-material for forming the final product and finally dried to obtain the correct deliverable moisture. The method of the invention, when applied to such processes enables control of the moisturizer and successively drying parameters in order to achieve the right quantity of moisture content in the final product. The flow speed of homogenizer depends on the viscosity of the product, and the system controls the amount of liquids pumped into the system. The present application includes a system that uses a device for measurement of moisture connected to a mixing machine, homogenizer, mixer and drier. This is depicted in FIG. 5. A moisture sensor is connected to a mixing machine or homogeniser, or a mixer and drier. It must be understood that the implementation of this example may include the use of multiple sensors. The moisture data collected in real time is mapped using neurofuzzy logic as is described above and with PID controls. This data is fed to a drier or to a moisture adding machine such as a liquid pump depending on the end user requirements and the data collected. As is evident, the real time enables addition or removal of moisture dependant on the moisture readings obtained from the moisture analyser(s).

EXAMPLE 6

Online Moisture Measurement of Bulk Goods

This example relates to moisture measurement of free flowing bulk goods such as grain, food products, fertilizer, salt, rice, sand, potato chips, sugar beet chips, gypsum, wood chips etc. The bulk goods are passed in round duct through moisture sensor as shown FIG. 7. In an alternative embodiment that is depicted in FIG. 8, the moisture sensor is placed in a pilot line, that is in parallel to the main line, and the sample of the material is passed through.

Figure 7:
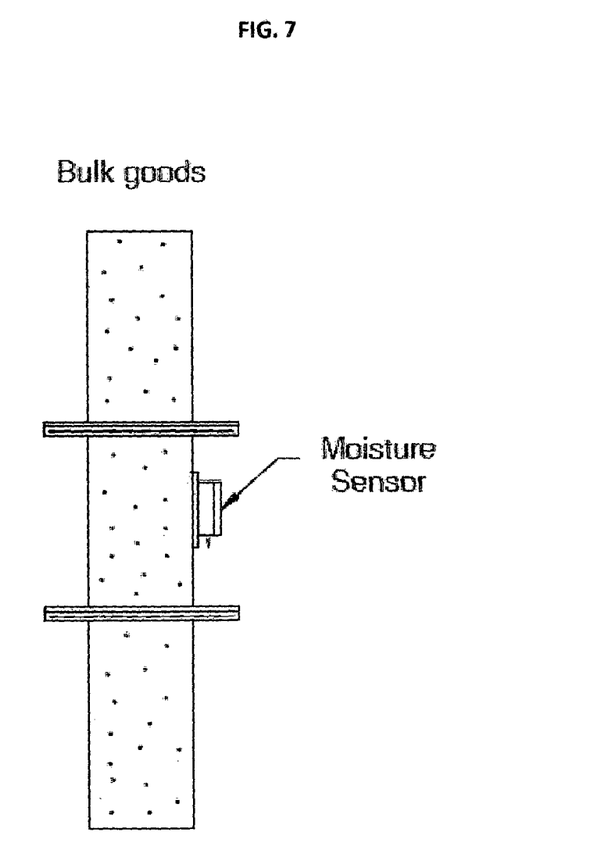
FIGS. 7 and 8 are a schematic depiction of the invention in relation to the measurement and control of moisture free flowing bulk goods. This is discussed in Example 6.
Figure 8:
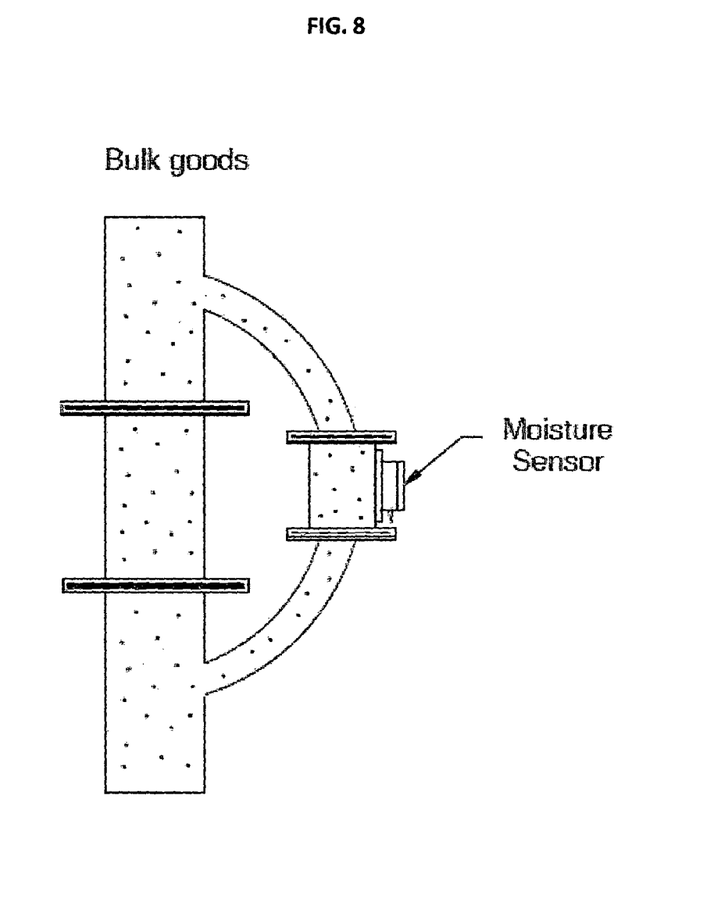

FIGS. 7 and 8 illustrate the control method and apparatus which includes a microprocessor, PLC or similar controller. The moisture sensor is interfaced directly with the production stream to regulate the speed of the sifter, the transportation, the extractor speed, water sprayers and/or other devices in the stream production line.

It must be understood that the device and control method of the invention is not limited by the foregoing disclosure or the examples, which only illustrate preferred embodiments. Variations and modifications are possible without departing from the spirit and scope of the invention in any manner.

We claim:

1. A method for on-line moisture determination and control in an industrial process for direct control of a drying process based on real-time measurement of moisture content of material being dried, said method comprising:
    (a) sensing moisture levels at one or more locations through dedicated sensing means to obtain sensed information;
    (b) collecting and collating the sensed information obtained in real time and in dynamic mode and transmitting the sensed information to a control means that is connected at one end to a moisture control mechanism;
    (c) processing the sensed information in the control means in real time to enable real time regulation of moisture content in the industrial process; and
    (d) wherein either the drying process is hastened to ensure greater drying or additional moisture is input based on processing of the sensed information in the control means.

2. The method as claimed in claim 1, wherein the moisture content of the material leaving the drying process is monitored and the operating parameters of a dehumidifier are controlled to maintain desired moisture content.

3. The method as claimed in claim 2, wherein controlled parameters are selected from the group consisting of dehumidified air volume, temperature and humidity supply to the hopper, volume and temperature of heated air supplied for reactivation of a desiccant material, and frequency of reactivation of the desiccant material.

4. The method as claimed in claim 2, wherein the operating parameters of the dehumidifier are adjusted based on the real-time measurement of the flow rate of material entering and/or leaving the drying process.

5. The method as claimed in claim 4, wherein the operation of the dehumidifier is adjusted in anticipation of a change in drying load due to the change in flow rate of the product material.

6. The method as claimed in claim 1, wherein the operating parameters of the dehumidifier are adjusted based on the real-time measurement of the moisture content of the material entering the drying process, thereby enabling adjustment of dehumidifier operation in anticipation of a change in drying load due to the change in moisture content of the entering material.

7. The method as claimed in claim 1, wherein the moisture content of the material is measured at one or more intermediate points during the drying process to adjust the drying parameters for optimum performance.

8. The method as claimed in claim 1, wherein real-time input data acquired are used in a comprehensive control algorithm for the dehumidifier and process air system.

9. The method as claimed in claim 8, wherein the input data and control algorithms is used to control a dehumidifier providing drying capacity to two or more parallel drying processes.

10. The method as claimed in claim 9, wherein the control comprises overall adjustment of the operation of the dehumidifier and process air system and individual adjustment of the drying force supplied to each drying process.

11. The method as claimed in claim 10, wherein said adjustment is selected from one or more of volume, power level and temperature of drying force provided.

12. The method as claimed in claim 1, wherein the values generated by sensors are utilised by the control means to minimise the power requirements of the process, using integral calculation of multiple parameters.

13. The method as claimed in claim 12, wherein the control process comprises control of one or more of temperature set point, drying time, dew point adjustment, air flow speed, rotor speed, nitrogen set point, nitrogen filtering station, desiccants tower switch, desiccant regeneration, microwave power generators, filters replacement time, methane gas regulation, and steam generator control.

14. The method as claimed in claim 1, wherein the process is used for bulk good drying, organic food industry, dyestuff industry, pharmaceutical manufacturing process, load control, and hopper operation.

15. The method for moisture measurement and control in a hopper operation for direct control of a drying process based on real-time measurement of moisture content of material in the hopper, wherein a load material is analysed to determine the moisture content using one or more moisture sensors, feeding the load material to one or more machinery interfaces, the data collected being mapped using one or more neurofuzzy controls following which drying parameters are set with a control means, followed by starting a drying cycle, discharging the product to the process, and dependent on data relating to moisture carrying out further drying or ending the drying process in real time.

16. A device for in-line real time moisture determination and control in an industrial process for direct control of a drying process based on real-time measurement of moisture content of material being dried, the device comprising at least one sensing means provided at least one predetermined location in the industrial process, said sensing means determining moisture level in the industrial process at such location in real time and in dynamic mode, that at least one sensing means being operatively associated to a control means to receive sensed information in real time and in dynamic mode for processing, said control means being provided with pre-determined optimal moisture level information, and capable of correlating moisture level inputs from said at least one sensing means, the control means being connected to a moisture control means and guiding said moisture control means to either input additional moisture or reduce moisture input to ensure greater drying dependent on the moisture level information received from the at least one sensing means.

17. The device as claimed in claim 16, wherein the device is applied to a drying system in a hopper, and comprising two sensors, the first sensor being provided at an inlet position of the dryer to provide information in respect of the average moisture content measured during loading of the material into the dryer, the second sensor being provided at an outlet position on the dryer to supply information on the moisture content after the drying process, a two-way valve being provided to allow the return of non-conforming material back to the dryer for a further period of drying if the measured value does not conform to the desired product.

18. The device as claimed in claim 16, for use in bulk good drying, organic food industry, dyestuff industry, pharmaceutical manufacturing process, load control, and hopper operation.

* * * * *